(12) United States Patent
Cauwet-Martin et al.

(10) Patent No.: US 6,514,488 B1
(45) Date of Patent: Feb. 4, 2003

(54) DETERGENT COSMETIC COMPOSITIONS AND USES THEREOF

(75) Inventors: Danièle Cauwet-Martin, Paris (FR); Serge Restle, Saint-Prix (FR); Claude Dubief, Le Chesnay (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/496,915

(22) Filed: Feb. 3, 2000

(30) Foreign Application Priority Data

Feb. 3, 1999 (FR) .............................. 99 01238

(51) Int. Cl.⁷ .................. A61K 7/06; A61K 7/08; A61K 7/09; A61K 7/15
(52) U.S. Cl. ................ 424/70.1; 424/70.11; 424/70.13; 424/70.15; 424/70.17; 424/70.21; 424/70.22; 424/70.27; 424/70.31
(58) Field of Search ................ 424/70.1, 70.11, 424/70.13, 70.17, 70.15, 70.21, 70.22, 70.27, 70.31

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,589,578 A | 6/1971 | Kamphausen |
| 3,874,870 A | 4/1975 | Green et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,131,576 A | 12/1978 | Iovine et al. |
| 4,710,374 A | 12/1987 | Grollier et al. |
| 4,719,099 A | 1/1988 | Grollier et al. |
| 4,985,239 A | 1/1991 | Yahagi et al. |
| 5,009,880 A | 4/1991 | Grollier et al. |
| 5,626,840 A | 5/1997 | Thomaides et al. |

FOREIGN PATENT DOCUMENTS

| | | |
|---|---|---|
| DE | 42 33 385 | 4/1994 |
| DE | 44 09 189 | 9/1995 |
| DE | 197 23 763 | 12/1998 |
| EP | 0 080 976 | 6/1983 |
| EP | 0 122 324 | 10/1984 |
| EP | 0 214 626 | 3/1987 |
| EP | 0 337 354 | 10/1989 |
| EP | 0 542 072 B1 | 5/1993 |
| EP | 0 542 072 | 5/1993 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 751 162 | 1/1997 |
| EP | 0 779 310 | 6/1997 |
| EP | 0 789 459 | 8/1997 |
| EP | 0 838 211 | 4/1998 |
| EP | 0 838 212 | 4/1998 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 743 297 | 7/1997 |
| FR | 2 745 175 | 8/1997 |
| FR | 2 745 176 | 8/1997 |
| FR | 2 749 506 | 12/1997 |
| FR | 2 756 488 | 6/1998 |
| WO | WO 94/03510 | 2/1994 |
| WO | WO 96/14049 | 5/1996 |
| WO | WO 96/14050 | 5/1996 |
| WO | WO 97/09031 | 3/1997 |

OTHER PUBLICATIONS

English language Abstract of EP 0 542 072 B1.
English language Derwent Abstract of EP 0 779 310.
English language Derwent Abstract of FR 1 583 363.
English language Derwent Abstract of FR 2 077 143.
English language Derwent Abstract of FR 2 080 759.
English language abstract of FR 2 162 025.

(List continued on next page.)

Primary Examiner—Thurman K. Page
Assistant Examiner—S. Tran
(74) Attorney, Agent, or Firm—Finnegan, Henderson, Farabow, Garrett & Dunner, L.L.P.

(57) ABSTRACT

The invention relates to novel detergent compositions, in particular hair compositions, containing in a cosmetically acceptable medium, a washing base, at least one cationic polymer and at least one anionic polycondensate containing at least one polyurethane and/or polyurea sequence, the polycondensate being water-soluble.

35 Claims, No Drawings

OTHER PUBLICATIONS

English language Derwent Abstract of FR 2 190 406.
English language Derwent Abstract of FR 2 252 840.
English language Derwent Abstract of FR 2 270 846.
English language Derwent Abstract of FR 2 280 361.
English language abstract of FR 2 316 271.
English language Derwent Abstract of FR 2 320 330.
English language Derwent Abstract of FR 2 336 434.
English language abstract of FR 2 368 508.
English language Derwent Abstract of FR 2 383 660.
English language abstract of FR 2 393 573.
English language abstract of FR 2 413 907.
English language abstract of FR 2 470 596.
English language abstract of FR 2 505 348.
English language abstract of FR 2 519 863.
English language abstract of FR 2 542 997.
English language Derwent Abstract of FR 2 598 611.
M.R. Porter, Handbook of Surfactants, Blackie & Son Ltd., 1991, pp. 116–178.
English language Derwent Abstract of DE 42 33 385.
English language Derwent Abstract of DE 44 09 189.
English language Derwent Abstract of DE 197 23 763.
English language Derwent Abstract of EP 0 080 976.
English language Derwent Abstract of EP 0 648 485.
English language Derwent Abstract of EP 0 656 021.
English language Derwent Abstract of FR 2 743 297.
English language Derwent Abstract of FR 2 745 175.
English language Derwent Abstract of FR 2 745 176.
English language Derwent Abstract of FR 2 749 506.
English language Derwent Abstract of FR 2 756 488.
English language Derwent Abstract of EP 0 637 600.
English language Derwent Abstract of EP 0 751 162.

DETERGENT COSMETIC COMPOSITIONS AND USES THEREOF

The present invention relates to novel cosmetic compositions with improved properties, intended simultaneously for cleansing, conditioning and styling keratin substances such as the hair, and comprising, in a cosmetically acceptable support, a washing base consisting of surfactants with detergent power, in which are also present cationic polymers in combination with a water-soluble anionic polyurea or a polyurethane. The invention also relates to the use of the compositions in the abovementioned cosmetic application.

It is common practice to use detergent hair compositions (or shampoos) based essentially on conventional surfactants of anionic, nonionic and/or amphoteric type in particular, more particularly of anionic type, for cleansing and/or washing the hair. These compositions are applied to wet hair and the lather generated by massaging or friction with the hands allows, after rinsing with water, the removal of the various types of soiling initially present on the hair.

Admittedly, these base compositions have good washing power, but the intrinsic cosmetic properties associated therewith are, nevertheless, fairly poor. In particular, the relatively aggressive nature of such a cleansing treatment can lead in the long run to more or less pronounced damage to hair fibers, associated in particular with the gradual removal of the lipids or proteins contained in or at the surface of these fibers.

Thus, to improve the cosmetic properties of the above detergent compositions, and more particularly of those which are intended to be applied to sensitized hair (i.e., hair which has been damaged or embrittled, in particular under the chemical action of atmospheric agents and/or of hair treatments such as permanent-waving, dyeing or bleaching operations), it is now common practice to introduce into these compositions additional cosmetic agents known as conditioners which are intended mainly to repair or limit the harmful or undesirable effects induced by the various treatments or aggressions to which hair fibers are subjected more or less repeatedly. Needless to say, these conditioners can also improve the cosmetic behaviour of natural hair.

The conditioners most commonly used to date in shampoos are cationic polymers, which give washed, dry or wet hair an ease of disentangling, a softness and a smoothness that are markedly improved when compared with that which might be obtained with the corresponding cleansing compositions which are free of these polymers.

Moreover, it has been sought for some time to obtain conditioning shampoos which are capable of giving washed hair not only the cosmetic properties mentioned above but also, to a more or less pronounced extent, the properties of styling, volume, shaping and hold. These washing shampoos with improved general cosmetic properties are often referred to for simplicity as "styling shampoos", and this expression will be adopted in the description hereinbelow.

However, despite the progress achieved recently in the area of styling shampoos based on cationic polymers, these shampoos are not really entirely satisfactory, such that a strong need still exists currently with regards having available novel products which have better performance characteristics as regards one or more of the cosmetic properties mentioned above. The present invention is directed towards satisfying such a need.

Thus, after considerable research conducted in this matter, it has now been found entirely surprisingly and unexpectedly, that by introducing an anionic polycondensate comprising at least one polyurethane and/or polyurea sequence as defined below, into detergent compositions, in particular hair compositions, containing cationic polymers, it is possible to substantially and significantly improve the cosmetic properties associated with these compositions, while at the same time retaining their good intrinsic washing power.

In the description and claims, the term "polyurethane" will be used as being equivalent to a polycondensate comprising at least one polyurethane and/or polyurea sequence.

Without wishing to limit the present invention to any theory, there would appear to be, during rinsing, specific interactions and/or affinities between the cationic polymers and anionic polyurethanes, in accordance with the invention, and the hair, which promote regular, appreciable and long-lasting deposition of the polyurethanes and cationic polymers onto the surface of the hair. This qualitative and quantitative deposition probably being one of the causes of the improvements observed as regards the final properties, in particular the ease of styling, the hold, the liveliness and volume of the treated hair. In any case, the cosmetic properties associated with the washing bases containing the combination of agents (cationic polymer/polyurethane) in accordance with the invention are markedly superior to those which can be obtained using only one of these agents at an equivalent overall concentration. All of these discoveries form the basis of the present invention.

Thus, according to the present invention, novel detergent compositions, in particular hair compositions, are now proposed, comprising, in a cosmetically acceptable medium, a washing base, at least one cationic polymer and at least one anionic polycondensate comprising at least one water-soluble polyurethane and/or polyurea sequence.

A subject of the invention is also the cosmetic use of the above compositions for cleansing, conditioning and styling keratin substances, in particular the hair.

However, other characteristics, aspects and advantages of the invention will emerge even more clearly on reading the description which follows, as well as the concrete, but in no way limiting, examples intended to illustrate it.

As mentioned above, the constituents forming part of the composition of the hair products of the invention are (i) at least one surfactant with detergent power intended to form the washing base, (ii) at least one cationic polymer and (iii) at least one water-soluble anionic polyurethane.

A-WASHING BASE

The compositions in accordance with the invention necessarily comprise a washing base, which is generally aqueous.

The surfactant(s) forming the washing base can either be chosen, alone or as mixtures, from anionic, amphoteric, nonionic, zwitterionic and cationic surfactants. However, according to the invention, the washing base preferably comprises anionic surfactants or mixtures of anionic surfactants and amphoteric surfactants or nonionic surfactants.

The minimum amount of washing base needed is that amount which is just sufficient to give the final composition a satisfactory foaming and/or detergent power, and excessive amounts of washing base do not really afford any additional advantages. Thus, according to the invention, the washing base is present in an amount ranging from 4% to 50% by weight, preferably from 6% to 25% by weight, and even more preferably from 8% to 20% by weight, relative to the total weight of the final composition.

The surfactants which are suitable for carrying out the present invention are, in particular, the following:
(i) Anionic Surfactant(s)

As examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; ($C_6$–$C_{24}$)alkyl sulphosuccinates, ($C_6$–$C_{24}$)alkyl ether sulphosuccinates, ($C_6$–$C_{24}$)alkylamide sulphosuccinates; ($C_6$–$C_{24}$)alkyl sulphoacetates; ($C_6$–$C_{24}$)acyl sarcosinates and ($C_6$–$C_{24}$)-acyl glutamates. It is also possible to use ($C_6$–$C_{24}$)-alkyl polyglycoside carboxylic esters such as alkylglucoside citrates, alkylpolyglycoside tartrates and alkylpolyglycoside sulphosuccinates; alkylsulphosuccinamates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; and acyl lactylates in which the acyl radical contains 8 to 20 carbon atoms. It is also possible to use alkyl-D-galactosiduronic acids and their salts, polyoxy-alkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, in particular those containing from 2 to 50 alkylene oxide groups in particular ethylene groups, and mixtures thereof.

Anionic surfactants comprising a carboxylic group are particularly preferred.

(ii) Nonionic Surfactant(s)

The nonionic surfactants are, themselves also, compounds that are well known per se (see in particular in this respect "Handbook of Surfactants" by M. R. Porter, published by Blackie & Son (Glasgow and London), 1991, pp. 116–178), the disclosure of which is hereby incorporated by reference, and, in the context of the present invention, their individual nature is not a critical feature. Thus, they can be chosen in particular from (non-limiting list) polyethoxylated, polypropoxylated or polyglycerolated fatty acids, alkylphenols, a-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; and fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s)

The amphoteric or zwitterionic surfactants, whose individual nature is not a critical feature in the context of the present invention, can be, in particular (non-limiting list), aliphatic secondary or tertiary amine derivatives in which the aliphatic radical is a linear or branched chain containing 8 to 18 carbon atoms and containing at least one water-soluble anionic group (for example, carboxylate, sulphonate, sulphate, phosphate or phosphonate); mention may also be made of ($C_8$–$C_{20}$)alkylbetaines, sulphobetaines, ($C_8$–$C_{20}$) alkylamido($C_1$–$C_6$)alkylbetaines and ($C_8$–$C_{20}$)alkylamido ($C_1$–$C_6$)alkylsulphobetaines.

Among the amine derivatives, mention may be made of the products sold under the name MIRANOL, as described in U.S. Pat. Nos. 2,528,378 and 2,781,354 and classified in the CTFA dictionary, 3rd edition, 1982, the disclosures of all of which are hereby incorporated by reference, under the names amphocarboxyglycinates and amphocarboxypropionates having the respective structures:

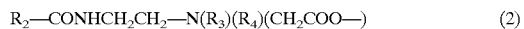

$$R_2\text{—CONHCH}_2\text{CH}_2\text{—N}(R_3)(R_4)(\text{CH}_2\text{COO—}) \quad (2)$$

in which:

$R_2$ is chosen from an alkyl radical of an acid $R_9$—COOH present in hydrolysed coconut oil, a heptyl, nonyl and undecyl radical, $R_9$ is a saturated or unsaturated, linear or branched ($C_5$–$C_9$) alkyl, $R'_3$ is a b-hydroxyethyl group, and $R_4$ is a carboxymethyl group;

and

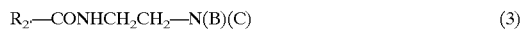

$$R_{2'}\text{—CONHCH}_2\text{CH}_2\text{—N(B)(C)} \quad (3)$$

in which:

B' is —$CH_2CH_2OX'$,

C' is —$(CH_2)_z$—Y', with z=1 or 2,

X' is chosen from a —$CH_2CH_2$—COOH group and a hydrogen atom,

Y' is chosen from a —COOH or the —$CH_2$—CHOH—$SO_3H$ radical, and $R_{2'}$ is an alkyl radical of an acid $R_9$—COOH present in coconut oil or in hydrolysed linseed oil, an alkyl radical, in particular a $C_7$, $C_9$, $C_{11}$ or $C_{13}$ alkyl radical, a $C_{17}$ alkyl radical and its iso form and an unsaturated $C_{17}$ radical.

$R_9$ is a saturated or unsaturated, linear or branched ($C_5$–$C_9$) alkyl,

These compounds are classified in the CTFA dictionary, 5th edition, 1993, the disclosure of which is hereby incorporated by reference, under the names disodium cocoamphodiacetate, disodium lauroamphodiacetate, disodium caprylamphodiacetate, disodium caprylloamphodiacetate, disodium cocoamphodipropionate, disodium lauroamphodipropionate, disodium caprylamphodipropionate, disodium caprylloamphodipropionate, lauroamphodipropionic acid, cocoamphodipropionic acid.

By way of example, mention may be made of the cocoamphodiacetate sold under the trade name MIRANOL® C2M concentrate by the company Rhodia Chimie.

In the compositions in accordance with the invention, mixtures of surfactants are preferably used, and in particular mixtures of anionic surfactants and mixtures of amphoteric or nonionic surfactants. A particularly preferred mixture is a mixture comprising at least one carboxylic anionic surfactant and at least one amphoteric or nonionic surfactant.

The anionic surfactant preferably used is chosen from polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)-alkylamido ether carboxylic acids and a mixture thereof with a sulphonated or sulphated surfactant such as sodium, triethanolamine or ammonium ($C_{12}$–$C_{14}$)alkyl sulphates, sodium ($C_{12}$–$C_{14}$) alkyl ether sulphates oxyethylenated with 2.2 mol of ethylene oxide, sodium cocoyl isethionate and mixtures thereof with:

either an amphoteric surfactant such as the amine derivatives known as disodium cocoamphodipropionate or sodium cocoamphopropionate, sold in particular by the company Rhodia Chimie under the trade name MIRANOL® C2M CONC. as an aqueous solution containing 38% active material, or under the name MIRANOL® C32;

or an amphoteric surfactant of zwitterionic type, such as alkylbetaines, in particular the cocoylbetaine sold under the name DEHYTON® AB 30 as an aqueous solution containing 32% AM by the company Henkel or alkylamidoalkylbetaines such as TEGOBETAINE® F50 sold by the company Goldschmidt, or a nonionic surfactant of alkylpolyglucoside type.

(iv) Cationic Surfactants

Among the cationic surfactants, mention may be made in particular (non-limiting list) of: salts of primary, secondary or tertiary fatty amines, which are if optionally polyoxyalkylenated; quaternary ammonium salts such as tetraalkylammonium, alkylamidoalkyl-trialkylammonium, trialkylbenzylammonium, trialkyl-hydroxyalkylammonium or alkylpyridinium chlorides or bromides; imidazoline derivatives; and amine oxides of cationic nature.

It will be noted that cationic surfactants, whose use is not excluded, do not constitute preferred surfactants for carrying out the present invention.

B-CATIONIC POLYMER(S)

The compositions in accordance with the invention also comprise a cationic polymer. The conditioners of cationic polymer type which can be used in accordance with the present invention can be chosen from any of those already known per se as enhancing the cosmetic properties of hair treated with detergent compositions, namely, in particular, those described in patent application EP-A-0,337,354 and in French patent applications FR-A-2,270,846, 2,383,660, 2,598,611, 2,470,596 and 2,519,863, the disclosures of all of which are hereby incorporated by reference.

Even more generally, for the purposes of the present invention, the expression "cationic polymer" denotes any polymer containing cationic groups and/or groups which can be ionized into cationic groups. The preferred cationic polymers are chosen from those which contain units containing primary, secondary, tertiary and/or quaternary amine groups which can either form part of the main polymer chain or which can be carried by a lateral substituent that is directly attached thereto. The cationic polymers generally used have a number-average molecular mass of from 500 to $5 \times 10^6$ approximately, and preferably from 1000 to $3 \times 10^6$ approximately.

Among the cationic polymers, mention may be made more particularly of polymers of polyquaternary ammonium, polyamino amide and polyamine type. These are known products.

The polymers of the polyquaternary ammonium, polyamino amide and polyamine type, which can be used in accordance with the present invention and which may be mentioned in particular, are those described in French Patent Nos. 2,505,348 or 2,542,997, the disclosures of both of which are hereby incorporated by reference. Among these polymers, mention may be made of the polymers set forth below.

(1) Homopolymers or copolymers derived from acrylic or methacrylic esters or amides and comprising at least one of the units of the following formulae:

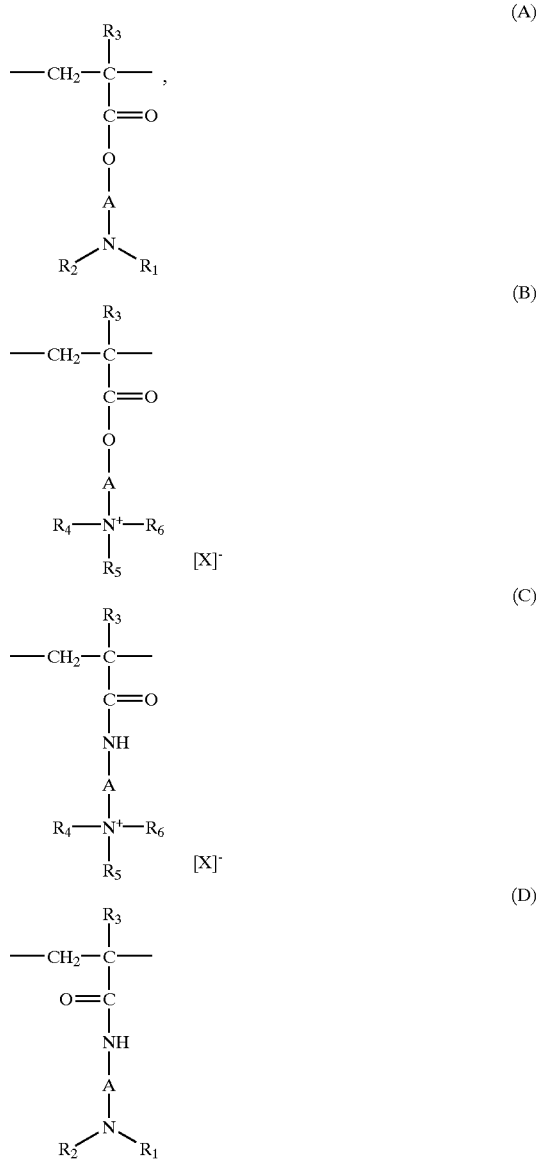

in which:

$R_3$, which may be identical or different, is chosen from a hydrogen atom and a $CH_3$ radical;

A, which may be identical or different, is chosen from a linear or branched alkyl group of 1 to 6 carbon atoms, preferably 2 or 3 carbon atoms, and a hydroxyalkyl group of 1 to 4 carbon atoms;

$R_4$, $R_5$ and $R_6$, which may be identical or different, are chosen from an alkyl group containing from 1 to 18 carbon atoms or a benzyl radical and preferably an alkyl group containing from 1 to 6 carbon atoms;

$R_1$ and $R_2$, which may be identical or different, are chosen from hydrogen and an alkyl group containing from 1 to 6 carbon atoms and preferably methyl or ethyl;

and

X is an anion derived from an inorganic or organic acid such as a methosulphate anion or halide such as chloride or bromide.

The copolymers of the family (1) can also contain one or more units derived from comonomers which can be chosen from the family of acrylamides, methacrylamides, diacetone acrylamides, acrylamides and methacrylamides substituted on the nitrogen with lower alkyls ($C_1$–$C_4$), acrylic or methacrylic acids or esters thereof, vinyllactams such as vinylpyrrolidone or vinylcaprolactam, and vinyl esters.

Thus, among these copolymers of family (1) mention may be made of:

- copolymers of acrylamide and of dimethylaminoethyl methacrylate quaternized with dimethyl sulphate or with a dimethyl halide such as that sold under the name HERCOFLOC by the company Hercules,
- copolymers of acrylamide and of methacryloyloxyethyltrimethylammonium chloride, described, for example, in patent application EP-A-080976, the disclosure of which is hereby incorporated by reference, and sold under the name BINA QUAT P 100 by the company Ciba Geigy,
- the copolymer of acrylamide and of methacryloyloxyethyltrimethylammonium methosulphate sold under the name RETEN by the company Hercules,
- quaternized or non-quaternized vinylpyrrolidone/ dialkylaminoalkyl acrylate or methacrylate copolymers, such as the products sold under the name GAFQUAT by the company ISP such as, for example, GAFQUAT 734 or GAFQUAT 755 or the products known as COPOLYMER 845, 958 and 937. These polymers are described in detail in French Patent Nos. 2,077,143 and 2,393,573, the disclosures of both of which are hereby incorporated by reference,
- dimethylaminoethyl methacrylate/vinylcaprolactam/ vinylpyrrolidone terpolymers, such as the product sold under the name GAFFIX VC 713 by the company ISP,
- the vinylpyrrolidone/methacrylamidopropyl dimethylamine copolymers sold in particular under the name STYLEZE CC 10 by ISP,
- and the quaternized vinylpyrrolidone/ dimethylaminopropyl methacrylamide copolymers such as the product sold under the name GAFQUAT HS 100 by the company ISP.

(2) The cellulose ether derivatives containing quaternary ammonium groups, described in French patent 1,492,597, the disclosure of which is hereby incorporated by reference, and in particular polymers sold under the names JR (JR 400, JR 125 and JR 30M) or LR (LR 400, or LR 30M) by the company Union Carbide Corporation. These polymers are also defined in the CTFA dictionary as quaternary ammoniums of hydroxyethylcellulose which have reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, the disclosure of which is hereby incorporated by reference, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to these cationic cellulose derivatives are more particularly the products sold under the names CELQUAT L 200 and CELQUAT H 100 by the company National Starch.

(4) The cationic polysaccharides described more particularly in U.S. Pat. Nos. 3,589,578 and 4,031,307, the disclosures of both of which are hereby incorporated by reference, such as guar gums containing cationic trialkylammonium groups. Guar gums modified with a salt (e.g., chloride) of 2,3-epoxypropyltrimethylammonium are used, for example.

Such products are sold in particular under the trade names JAGUAR C13 S, JAGUAR C 15, JAGUAR C 17 or JAGUAR C162 by the company Meyhall.

(5) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French Patent Nos. 2,162,025 and 2,280,361, the disclosures of which are hereby incorporated by reference.

(6) Water-soluble polyamino amides prepared in particular by polycondensation of an acidic compound with a polyamine. These polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent is used in proportions ranging from 0.025 to 0.35 mol per amine group of the polyamino amide. These polyamino amides can be alkylated or, if they contain one or more tertiary amine functions, they can be quaternized. Such polymers are described, in particular, in French Patent Nos. 2,252,840 and 2,368,508, the disclosures of which are hereby incorporated by reference.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1,583,363, the disclosure of which is hereby incorporated by reference.

Among these derivatives, mention may be made more particularly of the adipic acid/dimethylaminohydroxypropyl/diethylenetriamine polymers sold under the name CARTARETINE F, F4 or F8 by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is from 0.8:1 to 1.4:1. The polyamino amide resulting therefrom is reacted with epichlorohydrin in a molar ratio of epichlorohydrin relative to the secondary amine group of the polyamino amide of from 0.5:1 to 1.8:1. Such polymers are described in particular in U.S. Pat. Nos. 3,227,615 and 2,961,347, the disclosures of which are hereby incorporated by reference.

Polymers of this type are sold in particular under the name HERCOSETT 57 by the company Hercules Inc. or alternatively under the name PD 170 or DELSETTE 101 by the company Hercules in the case of the adipic acid/ epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formulae (VI) or (VI'):

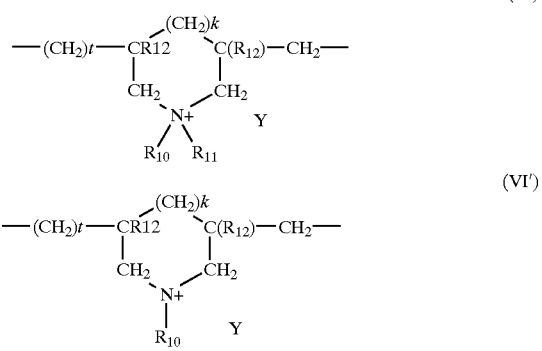

in which:

k and t are equal to 0 or 1, the sum k+t being equal to 1;

$R_{12}$ is chosen from a hydrogen atom and a methyl radical;

$R_{10}$ and $R_{11}$, which may be the same or different, are chosen from an alkyl group having from 1 to 22 carbon atoms, a hydroxyalkyl group in which the alkyl group preferably has 1 to 5 carbon atoms, or a lower amido-($C_1$–$C_4$)alkyl group, or $R_{10}$ and $R_{11}$ can denote, together with the nitrogen atom to which they are attached, heterocyclic groups such as piperidyl or morpholinyl;

$Y^-$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406, the disclosures of which are hereby incorporated by reference.

$R_{10}$ and $R_{11}$, which may be the same or different, preferably are chosen from an alkyl group containing from 1 to 4 carbon atoms.

Among the polymers defined above, mention may be made more particularly of the dimethyidiallylammonium chloride homopolymer sold under the name MERQUAT 100 by the company Calgon and its homologues of low weight-average molecular mass and copolymers of diallyldimethylammonium chloride and of acrylamide sold under the name MERQUAT 550.

(10) The quaternary diammonium polymer containing repeating units corresponding to the formula:

in which:

$R_{13}$, $R_{14}$, $R_{15}$ and $R_{16}$, which may be identical or different, are chosen from aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_6$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene and D is a quaternary ammonium group;

$A_1$ and $B'_1$ which may be identical or different, are chosen from polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ is an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH_2)_n$—CO—D—OC—$(CH_2)_n$— in which n is an integer from 1 to 6, and

D is chosen from:

a) a glycol residue of formula: —O—Z—O—, where Z is chosen from a linear or branched hydrocarbon radical or a group corresponding to one of the following formulae:

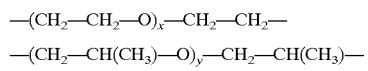

where x and y are chosen from an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y is chosen from a linear or branched hydrocarbon radical, and alternatively the divalent radical

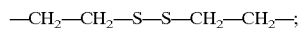

d) a urylene group of formula: —NH—CO—NH—.

Preferably, $X^-$ is an anion such as chloride or bromide.

These polymers generally have a number-average molecular mass of from 1000 to 100,000.

Polymers of this type are described in particular in French Patent Nos. 2,320,330, 2,270,846, 2,316,271, 2,336,434 and 2,413,907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of all of which are hereby incorporated by reference.

It is more particularly possible to use the polymers consisting of repeating units corresponding to the formula:

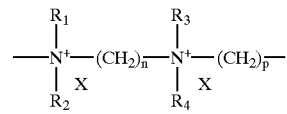

in which:

$R_1$, $R_2$, $R_3$ and $R_4$, which may be identical or different, are chosen from an alkyl or hydroxyalkyl radical containing from 1 to 4 carbon atoms approximately, n and p are integers ranging from 2 to 20 approximately, and X⁻ is an anion derived from an inorganic or organic acid.

One compound of formula (a) which is particularly preferred is the one for which $R_1$, $R_2$, $R_3$ and $R_4$ represent a methyl radical and n=3, p=6 and X=Cl, referred to as hexadimethrine chloride according to the INCI (CTFA) nomenclature.

(11) Quaternary polyammonium polymers consisting of units of formula (VIII):

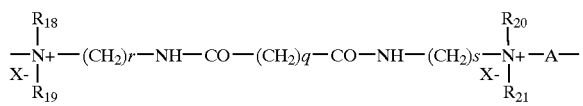

(VIII)

in which formula:

$R_{18}$, $R_{19}$, $R_{20}$ and $R_{21}$, which may be identical or different, are chosen from a hydrogen atom or a methyl, ethyl, propyl, b-hydroxyethyl, b-hydroxypropyl and —$CH_2CH_2(OCH_2CH_2)_pOH$ radical, where p is equal to 0 or to an integer from 1 to 6, with the proviso that $R_{18}$, $R_{19}$, $R_{20}$ and $R_{21}$ do not simultaneously represent a hydrogen atom, r and s, which may be identical or different, are integers from 1 to 6, q is equal to 0 or to an integer between 1 and 34, X is a halogen atom, and A is chosen from a dihalide radical and preferably the radical —$CH_2$—$CH_2$—O—$CH_2$—$CH_2$—.

Such compounds are described in particular in patent application EP-A-122,324, the disclosure of which is hereby incorporated by reference.

Among these products, mention may be made, for example, of MIRAPOL A 15, MIRAPOL AD1, MIRAPOL AZ1 and MIRAPOL 175 sold by the company Miranol.

(12) Quaternary polymers of vinylpyrrolidone and of vinylimidazole, such as, for example, the products sold under the names LUVIQUAT FC 905, FC 550 and FC 370 by the company BASF.

(13) Polyamines such as POLYQUART H sold by Henkel under the reference name "Polyethylene glycol (15) tallow polyamine" in the CTFA dictionary.

(14) Crosslinked polymers of methacryloyloxy($C_1$–$C_4$) alkyltri($C_1$–$C_4$)-alkylammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of the copolymer in mineral oil can be used more particularly. This dispersion is sold under the name SALCARE® SC 92 by the company Allied Colloids. A crosslinked methacryloyloxyethyltrimethylammonium chloride homopolymer containing about 50% by weight of the homopolymer in mineral oil or in a liquid ester can also be used. These dispersions are sold under the names SALCARE® SC 95 and SALCARE® SC 96 by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which can be used in the context of the present invention, it is preferred to use quaternary cellulose ether derivatives such as the products sold under the name JR 400 by the company Union Carbide Corporation, cyclopolymers, in particular the polymers or copolymers of dimethyldiallylammonium chloride and of acrylamide, sold under the names MERQUAT 100, MERQUAT 550 and MERQUAT S by the company Calgon, cationic polysaccharides such as the guar gums modified with 2,3-epoxypropyltrimethylammonium chloride sold under the name JAGUAR C13S by the company Meyhall and the vinylpyrrolidone/methacrylamidopropyldimethylamine copolymers sold in particular under the name STYLEZE CC 10 by the company ISP, and mixtures thereof.

According to the invention, the cationic polymer(s) can represent from 0.01% to 10% by weight, preferably from 0.05% to 5% by weight and even more preferably from 0.1% to 3% by weight, relative to the total weight of the final composition.

C-Polyurethanes and/or Polyureas

According to one characteristic of the detergent hair compositions in accordance with the invention, they also contain at least one polycondensate comprising at least one polyurethane and/or polyurea sequence, the polycondensate being water-soluble.

The polycondensates comprising at least one polyurethane and/or polyurea sequence to which the present invention is particularly directed are those described in patents EP 0,751,162, EP 0,637,600, FR 2,743,297 and EP 0,648,485, of which L'Oréal is the proprietor, as well as patents EP 0,656,021 or WO 94/03510 from the company BASF and EP 0,619,111 from the company National Starch, the disclosures of all of which are hereby incorporated by reference.

The polycondensates used in accordance with the invention are water-soluble, either in the acid form or after partial or total neutralization with an organic or inorganic base. The water-soluble polymers according to the present invention are those which give, when dissolved in water, compositions that are clear to the naked eye (at a concentration at least equal to 1% of active material and at room temperature (20–25° C.)).

By way of example, the polycondensate can be formed by an arrangement of blocks, this arrangement being obtained in particular from:

(1) at least one compound which contains two or more than two active hydrogen atoms per molecule;

(2) at least one diol or a mixture of diols containing acid radicals or salts thereof; and (3) at least one di- or polyisocyanate.

Advantageously, the compounds (1) are chosen from the group comprising diols, diamines, polyesterols, polyetherols or a mixture thereof.

The compounds (1) which are preferred are linear polyethylene and polypropylene glycols, in particular those obtained by reaction of ethylene oxide or propylene oxide with water or diethylene glycol or dipropylene glycol in the presence of sodium hydroxide as catalyst. These polyglycols generally have a molecular weight from about 600 to 20,000.

Other preferred organic compounds are those which contain mercapto, amino, carboxyl or hydroxyl groups. Among these, mention may be made more particularly of polyhydroxy compounds such as polyether diols, polyester diols, polyacetal diols, polyamide diols, polyester polyamide diols, poly(alkylene ether) diols, polythioether diols and polycarbonate diols.

The preferred polyether diols are, for example, the products of condensation of ethylene oxide, of propylene oxide or of tetrahydrofuran, the grafted or block copolymerization or condensation products thereof, such as mixtures of ethylene ioxide and propylene oxide condensates, and products of polymerization of olefins, under high pressure, with alkylene oxide condensates. Suitable polyethers are prepared, for example, by condensation of alkylene oxides and polyhydric alcohols, such as ethylene glycol, 1,2-propylene glycol and 1,4-butanediol.

The polyester diols, polyester amides and polyamide diols are preferably saturated and are obtained, for example, from the reaction of saturated or unsaturated polycarboxylic acids with polyhydric alcohols, diamines or polyamines. Adipic acid, succinic acid, phthalic acid, isophthalic acid, terephthalic acid and maleic acid can be used, for example, to prepare these compounds. Suitable polyhydric alcohols for preparing the polyesters include, for example, ethylene glycol, diethylene glycol, 1,2-propylene glycol, 1,4-butanediol, neopentyl glycol and hexanediol. Amino alcohols, for example ethanolamine can also be used. Suitable diamines for preparing the polyester amides are ethylenediamine and hexamethylenediamine.

Suitable polyacetals can be prepared, for example, from 1,4-butanediol or hexanediol and formaldehyde. Suitable polythioethers can be prepared, for example, by condensation reaction between thioglycols either alone or in combination with other glycols such as ethylene glycol, 1,2-propylene glycol or with other polyhydroxylated compounds. Polyhydroxylated compounds already containing urea or urethane groups, natural polyols, which can be further modified, for example castor oil and carbohydrates, can also be used.

More preferably, the compound of group (1) is a polyesterol, in particular a polyester diol formed by the reaction of at least one (di)polyol ($1_a$) and of at least one acid ($1_b$). The (di)polyol ($1_a$) is chosen in particular from the group comprising neopentyl glycol, 1,4-butanediol, hexanediol, ethylene glycol, diethylene glycol, propylene glycol, butylene glycol, neopentyl glycol and (di) polyethylene glycol. The acid ($1_b$) is chosen in particular from the group comprising phthalic acid, isophthalic acid, adipic acid and (poly)lactic acid.

The compounds (2) which may be used in particular are a hydroxycarboxylic acid such as dimethylolpropanoic acid (DMPA) or a 2,2-hydroxymethylcarboxylic acid. In general, the compound (2) is useful as a coupling block.

The compounds (2) which are particularly preferred in accordance with the invention are those chosen from the group comprising 2,2-di(hydroxymethyl)-acetic acid, 2,2-dihydroxymethylpropionic acid, 2,2-dihydroxymethylbutyric acid and 2,2-dihydroxymethylpentanoic acid.

The di- or polyisocyanate (3) can be chosen in particular from the group comprising hexamethylene diisocyanate, isophorone diisocyanate (IPDI), tolylene diisocyanate, diphenylmethane 4,4'-diisocyanate (DPMD) and dicyclohexylmethane 4,4'-diisocyanate (DCMD), methylenebis(p-phenyl) diisocyanate, methylenebis(4-cyclohexyl isocyanate), toluene diisocyanate, 1,5-naphthalene diisocyanate, 4,4'-diphenylmethane diisocyanate, 2,2'-dimethyl-4,4'-diphenyl methane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane 1,4-diisocyanate, hexane 1,6-diisocyanate and cyclohexane 1,4-diisocyanate.

The polycondensate can be formed using an additional compound (4) which generally serves to lengthen the polycondensate chain. These compounds (4) can be chosen from the group comprising, in particular, saturated or unsaturated glycols such as ethylene glycol, diethylene glycol, neopentyl glycol, triethylene glycol, amino alcohols such as ethanolamine, propanolamine or butanolamine, heterocyclic, aromatic, cycloaliphatic and aliphatic primary amines, diamines, carboxylic acids such as aliphatic, aromatic and heterocyclic carboxylic acids, for instance oxalic acid, succinic acid, glutaric acid, adipic acid, sebacic acid or terephthalic acid, and aminocarboxylic acids. The preferred compounds (4) are aliphatic diols.

An anionic polyurethane which is particularly preferred is polyurethane-1 (INCI name) sold by BASF under the name LUVISET PURE.

The polycondensates in accordance with the invention can also be formed from additional compounds (5) having a silicone skeleton, such as polysiloxanes, polyalkylsiloxanes or polyarylsiloxanes, in particular polyethylsiloxanes, polymethylsiloxanes and polyphenylsiloxanes, optionally comprising hydrocarbon-based chains grafted onto silicon atoms.

The polyurethane and/or polyurea sequences of the polymer which are used advantageously contain a base repeating unit corresponding to the general formula below:

$$—X'—B—X'—CO—NH—R—NH—CO— \quad (I')$$

in which:

the radicals X', which may be identical or different, are chosen from O and NH,

B is a divalent hydrocarbon-based radical, this radical being substituted or unsubstituted, and R is a divalent radical chosen from alkylene radicals of aromatic, ($C_1$ to $C_{20}$) aliphatic or ($C_1$ to $C_{20}$) cycloaliphatic type, these radicals being substituted or unsubstituted.

Preferably, the radical B is a ($C_1$ to $C_{30}$) radical and bears a group containing one or more carboxylic function(s) and/or one or more sulphonic function(s), the said carboxylic and/or sulphonic functions being in free form or else partially or totally neutralized with an inorganic or organic base.

The radical R is advantageously chosen from the radicals corresponding to the following formulae:

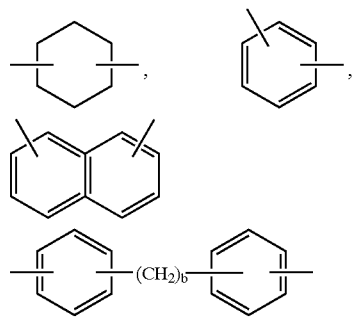

-continued

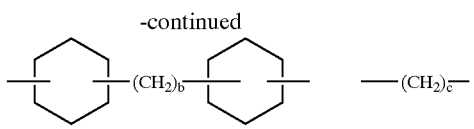

in which:
- b is an integer from 0 to 3 and c is an integer from 1 to 20, preferably from 2 to 12. In particular, the radical R is chosen from hexamethylene, 4,4'-biphenylenemethane, 2,4- and/or 2,6-tolylene, 1,5-naphthylene, p-phenylene and methylene4,4-bis (cyclohexyl) radicals and the divalent radical derived from isophorone.

The polycondensate used in accordance with the invention comprising at least one polyurethane and/or polyurea sequence can advantageously also comprise at least one polysiloxane sequence in which the base repeating unit corresponds, for example, to the general formula (II') below:

in which:
- P is a polysiloxane segment,
- the radicals X', which may be identical or different, are chosen from O and NH, and
- R is a divalent radical chosen from alkylene radicals of aromatic, $C_1$ to $C_{20}$ aliphatic or $C_1$ to $C_{20}$ cycloaliphatic type, these radicals being substituted or unsubstituted.

Advantageously, the polysiloxane segment P corresponds to the general formula below:

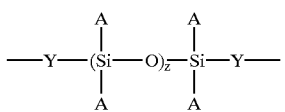

in which:
- the radicals A, which may be identical or different, are chosen, on the one hand, from $C_1$ to $C_{20}$ monovalent hydrocarbon-based radicals which are free or substantially free of ethylenic unsaturation, and, on the other hand, from aromatic radicals,
- Y is a divalent hydrocarbon-based radical, and
- z is an integer chosen such that the average molecular weight of the polysiloxane segment is from 300 to 10,000.

In general, the divalent radical Y is chosen from alkylene radicals of formula $-(CH_2)_a-$, in which a represents an integer which can be from 1 to 10.

The radicals A can be chosen from alkyl radicals, in particular methyl, ethyl, propyl, isopropyl, butyl, pentyl, hexyl, octyl, decyl, dodecyl and octadecyl radicals, cycloalkyl radicals, in particular a cyclohexyl radical, aryl radicals, in particular phenyl and naphthyl, arylalkyl radicals, in particular benzyl and phenylethyl, as well as tolyl and xylyl radicals.

The hair compositions in accordance with the invention contain the polyurethanes (polycondensates) defined above in weight contents which can be from 0.05% to 10%, preferably from 0.1% to 5%, relative to the total weight of the composition.

Generally, the cationic polymer/polyurethane ratio is from 0.001:1 to 200:1, preferably from 0.02:1 to 50:1, and even more particularly from 0.1:1 to 20:1.

The cosmetically acceptable aqueous medium can consist solely of water or of a mixture of water and a cosmetically acceptable solvent such as a $(C_1-C_4)$ lower alcohol, for instance ethanol, isopropanol, tert-butanol or n-butanol; alkylene glycols such as propylene glycol, and glycol ethers.

The detergent compositions according to the invention have a final pH generally of from 3 to 10. Preferably, this pH is from 4 to 9. Adjustment of the pH to the desired value can be carried out conventionally by adding a base (organic or inorganic base) to the composition, for example aqueous ammonia or a primary, secondary or tertiary (poly)amine such as monoethanolamine, diethanolamine, triethanolamine, isopropanolamine or 1,3-propanediamine, or alternatively by adding an inorganic or organic acid, preferably carboxylic acid such as, for example, citric acid.

The compositions in accordance with the invention can contain, in addition to the combination defined above, viscosity modifiers such as electrolytes, or thickeners. Mention may be made in particular of sodium chloride, sodium xylenesulphonate, scleroglucanes, xanthan gums, fatty acid alkanolamides, alkyl ether carboxylic acid alkanolamides optionally oxyethylenated with up to 5 mol of ethylene oxide, such as the product sold under the name AMINOL A5 by the company Chem Y, crosslinked polyacrylic acids and crosslinked acrylic acid/($C_{10}-C_{30}$) alkyl acrylate copolymers. These viscosity regulators are used in the compositions according to the invention in proportions which can range up to 10% by weight relative to the total weight of the composition.

The compositions in accordance with the invention can also contain up to 5% of pearlescent agents or opacifiers that are well known in the state of the art, such as, for example, ($C_{16}$) higher fatty alcohols, sodium or magnesium palmitate, sodium or magnesium stearate or hydroxystearate, acyl derivatives containing a fatty chain, such as the monostearates or distearates of ethylene glycol or of polyethylene glycol, and ethers containing a fatty chain such as, for example, distearyl ether or 1-(hexadecyloxy)-2-octadecanol.

Needless to say, the detergent compositions according to the invention can also contain any adjuvant commonly encountered in shampoos, such as, for example, fragrances, preserving agents, sequestering agents, thickeners, softeners, foam modifiers, dyes, pearlescent agents, moisturizers, antidandruff agents, anti-seborrhoeic agents, sunscreens and the like.

The compositions in accordance with the invention can optionally also contain other agents which have an effect of improving the cosmetic properties of the hair or the skin without, however, adversely affecting the stability of the compositions. Mention may be made in this respect of cationic surfactants, anionic or nonionic or amphoteric polymers, proteins, protein hydrolysates, ceramides, pseudoceramides, fatty acids containing linear or branched ($C_{18}-C_{40}$) chains, such as 18-methyleicosanoic acid, hydroxy acids, vitamins, panthenol, volatile or non-volatile silicones, which are soluble or insoluble in the medium, plant oils, synthetic oils and mixtures thereof.

The compositions according to the invention can also contain foam synergists such as ($C_{10}-C_{18}$) 1,2-alkanediols or fatty alkanolamides derived from mono- or diethanolamine.

Needless to say, a person skilled in the art will take care to select this or these optional additional compound(s) and/or the amounts thereof such that the advantageous properties intrinsically associated with the combination (washing base+cationic polymer+polyurethane according to the invention) in accordance with the invention are not, or are not substantially, adversely affected by the addition(s) envisaged.

These compositions can be in the form of more or less thickened liquids, creams or gels and they are mainly suitable for washing, caring for and/or styling the hair.

When the compositions in accordance with the invention are used as conventional shampoos, they are simply applied to wet hair and the lather generated by massaging or friction with the hands is then removed, after optionally leaving the shampoo on the hair for a period of time, by rinsing with water, it being possible for the operation to be repeated one or more times.

As indicated above, the compositions in accordance with the invention give the hair, after rinsing, a noteworthy styling effect which is manifested in particular by an ease of styling and of hold, as well as providing markedly improved volume and lightness.

A subject of the invention is also a process for washing and conditioning keratin substances such as the hair, which consists in applying an effective amount of a composition as defined above to the wet substances, followed by rinsing with water after optionally leaving the composition on the hair for a period of time.

Concrete but in no way limiting examples illustrating the invention will now be given.

In the examples, the following compounds are used:
LUVISET PURE (BASF) polyurethane-1 (INCI name) as an aqeuous-alcoholic solution containing 30% active material are water-soluble polyurethane;
AVALURE UR 450 (Goodrich) propylene glycol/ isophorone diisocyanate/ dimethylolpropanoic acid copolymer as an aqueous dispersion containing 38% active material, are water-insoluble polyurethane
AKYPOSOFT 45 NV (KAO) sodium lauryl ether carboxylate containing 4.5 mol of ethylene oxide as an aqueous solution containing 22% active material
AG 10 LK (KAO) ($C_8/C_{11}$) alkyl polyglucoside (1.4) as an aqueous solution containing 40% active material
282930 (National Starch) vinyl acetate/crotonic acid/vinyl neodecanoate terpolymer
STYLEZE CC 10 (ISP) vinylpyrrolidone/ methacrylamidopropyidimethylamine copolymer (80/20 by weight) as an aqueous solution containing 10% active material
MERQUAT 100 (Calgon) diallyidimethylammonium chloride homopolymer as an aqueous solution containing 40% active material
MERQUAT 550 (Calgon) diallyldimethylammonium chloride/acrylamide copolymer 50/50 (by weight) as an aqueous solution containing 8% active material.
JAGUAR C 13 S (Rhodia Chimie) hydroxypropylguar trimethylammonium chloride.
DEHYTON AB 30 (Henkel) cocoylbetaine as an aqueous solution containing 30% active material.

EXAMPLE 1

Two shampoo compositions were prepared, one in accordance with the invention (composition A) and the other comparative (composition B), differing from each other simply by the nature of the anionic polymer used:

|  | A (invention) | B |
| --- | --- | --- |
| AKYPOSOFT 45 NV (KAO) | 12 g AM | 12 g AM |
| AG 10 LK (KAO) | 2 g AM | 2 g AM |
| NaCl | 2 g | 2 g |

-continued

|  | A (invention) | B |
| --- | --- | --- |
| STYLEZE CC 10 (ISP) | 1 g AM | 1 g AM |
| LUVISET PURE (BASF) | 3 g AM | — |
| 282930 (National Starch) | — | 3 g AM |
| water qs | 100 g | 100 g |
| pH adjusted to | 6.9 | 6.9 |
| Appearance of the compositions | transparent | cloudy |

2.5 g locks of natural hair 27 cm long were premoistened and then placed in contact with 1 g of composition A according to the invention for 5 minutes, followed by rinsing with water. The locks were then dried under a hood for 20 minutes at 65° C. The process was performed using the same procedure as above with the comparative composition B.

Evaluation of the Feel of the Locks

A panel of 10 testers was presented with the locks prepared as indicated above.

They were requested to indicate the locks which they consider to be softer and smoother.

The 10 judges were unanimous and declared that the hair treated with composition A was softer and smoother.

Evaluation of the Fixing Properties

The expression "fixing properties" means the cohesion provided to a body of hair by depositing a material which limits the relative displacement of the hair as well as the stability over time of the body of hair formed.

A simple means for determining these properties consists in studying the relaxation of locks.

For this, 2.5 g locks of natural hair of length $L_0$ 27 cm were premoistened and then placed in contact with 1 g of composition A according to the invention for 5 minutes, followed by rinsing with water. The locks were then wound onto rollers of diameter 2 cm and length 7 cm, while still wet. The locks were then dried for 20 minutes under a drying hood. After drying, the locks were released from the rollers with care and suspended via their attachment to a fixed support such that the hair hangs freely under its own weight.

The process was performed using the same procedure as above with the comparative composition B.

The length (L) of the wound locks suspended via their own weight was then measured in front of a graduated panel.

The locks were then allowed to relax, still in the suspended state, for up to 4 hours at room temperature.

The length of the suspended locks then increased by a certain length (DL). The shorter this elongation DL the better the hold of the hairstyle over time.

|  | A (invention) |  | B |  |
| --- | --- | --- | --- | --- |
| LT0 | 12.6 | 10.8 | 12 | 13.5 |
| LT2 | 15 | 13.5 | 15 | 16.5 |
| LT4 | 15.5 | 14 | 15.5 | 17 |
| % elongation at 2 H | 19.0 | 25.0 | 25.0 | 22.2 |
| average of 2 H |  | 22 |  | 23.6 |
| % elongation at 4 H | 23.0 | 29.6 | 29.1 | 25.9 |
| average of 4 H |  | 26.3 |  | 27.5 |

With composition B, the elongation at 2 hours was 3 cm (average for 2 locks), whereas it was only 2.55 cm (average for 2 locks) for composition A, i.e., an improvement in the reduction of the elongation by more than 15%. At four hours, the elongation with composition B was 4.01 cm (average for 2 locks), while it was only 3.05 cm (average for 2 locks) for composition A. Thus, these results clearly reflects the better holding of the hairstyle obtained by means of the shampoo according to the invention.

EXAMPLE 2

Two shampoo compositions were prepared, one in accordance with the invention (composition A) and the other comparative (composition C), differing from each other simply by the solubility of the anionic polyurethane used:

|  | A (invention) | C |
|---|---|---|
| AKYPOSOFT 45 NV (KAO) | 12 g AM | 12 g AM |
| AG 10 LK (KAO) | 2 g AM | 2 g AM |
| NaCl | 2 g | 2 g |
| STYLEZE CC 10 (ISP) | 1 g AM | 1 g AM |
| LUVISET PURE (BASF) | 3 g AM | — |
| AVALURE UR 450* (Goodrich) | — | 3 g AM |
| water qs | 100 g | 100 g |
| pH adjusted to | 6.9 | 6.9 |
| Appearance of the compositions | transparent | cloudy |

AVALURE UR 450 is a water-insoluble anionic polyurethane.

2.5 g locks of natural hair 27 cm long were premoistened and then placed in contact with 1 g of composition A according to the invention for 5 minutes, followed by rinsing with water. The locks were then dried under a hood for 20 minutes at 65° C. The process was performed using the same procedure as above with the comparative composition C.

Evaluation of the Feel of the Locks

A panel of 10 testers was presented with the locks prepared as indicated above.

They were requested to indicate the locks which they consider to be softer and smoother.

The 10 judges were unanimous and declare that the hair treated with composition A was softer and smoother.

Evaluation of the Fixing Properties

The process was performed in the same way as in Example 1.

The length of the suspended locks then increased by a certain length (DL).

The smaller this elongation DL the better the hold of the hairstyle over time.

|  | A (invention) |  | B |  |
|---|---|---|---|---|
| LT0 | 12.6 | 10.8 | 11.8 | 12.0 |
| LT2 | 15 | 13.5 | 15.5 | 15.5 |
| LT4 | 15.5 | 14 | 16 | 16 |
| % elongation at 2 H | 19.0 | 25.0 | 31.3 | 29.2 |
| average of 2 H | 22 |  | 30.2 |  |
| % elongation at 4 H | 23.0 | 29.6 | 35.6 | 33.3 |
| average of 4 H | 26.3 |  | 34.4 |  |

With composition C, the elongation at 2 hours was 3.6 cm (average for 2 locks), whereas it was only 2.55 cm (average for 2 locks) for composition A, i.e., an improvement in the reduction of the elongation by more than 29%. At four hours, the elongation with composition C was 4.1 cm (average for 2 locks), while it was only 3.05 cm (average for 2 locks) for composition A. Thus, these results clearly which clearly reflects the better hold of the hairstyle obtained by means of the shampoo according to the invention.

EXAMPLE 3

A shampoo in accordance with the invention having the composition below was prepared:

| AKYPOSOFT 45 NV (KAO) | 12 g AM |
|---|---|
| AG 10 LK (KAO) | 2 g AM |
| STYLEZE CC-10 (ISP) | 1 g AM |
| LUVISET PURE (BASF) | 1.23 g AM |
| sodium chloride | 2 g |
| Water qs | 100 g |
| pH adjusted to | 7 |

EXAMPLE 4

A shampoo in accordance with the invention having the composition below was prepared:

| sodium lauryl ether sulphate (2.2 EO) | 15.5 g AM |
|---|---|
| cocoylbetaine (DEHYTON AB 30 from Henkel) | 2.4 g AM |
| JAGUAR C 13 S (Rhodia) | 0.05 g AM |
| LUVISET PURE (BASF) | 1 g AM |
| polydimethylsiloxane | 2.7 g AM |
| 1-(hexadecyloxy)-2-octadecanol/ cetyl alcohol | 2.5 g AM |
| coconut acid monoisopropanolamide | 1 g AM |
| sodium cetostearyl sulphate | 0.75 g AM |
| preserving agent qs |  |
| water qs | 100 g |
| pH adjusted to | 7 |

EXAMPLE 5

A shampoo in accordance with the invention having the composition below was prepared:

| BEAUFLIGHT SHAA (Sanyo Kasei) | 3 g AM |
|---|---|
| AG 10 LK (KAO) | 12 g AM |
| MERQUAT 100 from Calgon | 1 g AM |
| LUVISET PURE (BASF) | 3 g AM |
| sodium chloride | 1.5 g |
| oxyethylenated methyl glucoside dioleate (120 EO) | 1 g AM |
| water qs | 100 g |
| pH adjusted (NaOH/HCl) | 7 |

EXAMPLE 6

A shampoo in accordance with the invention having the composition below was prepared:

| BEALULIGHT SHAA (Sanyo Kasei) | 4.5 g AM |
|---|---|
| AG 10 LK (KAO) | 6 g AM |
| STYLEZE CC 10 (ISP) | 1 g AM |
| LUVISET PURE (BASF) | 4.05 g AM |
| sodium chloride | 1.5 g |
| oxyethylenated methyl glucoside dioleate (120 EO) | 1.5 g |
| water qs | 100 g |
| pH adjusted (NaOH/HCl) | 7 |

What is claimed is:

1. A detergent composition, comprising:
   at least one washing base,
   at least one cationic polymer,
   at least one anionic polycondensate comprising at least one polyurethane, at least one polyurea sequence, or mixtures thereof, said at least one anionic polycondensate being water-soluble.

2. A composition according to claim 1, wherein said composition comprises a cosmetically acceptable medium.

3. A composition according to claim 1, wherein said at least one washing base comprises at least one surfactant chosen from anionic surfactants, amphoteric surfactants, nonionic surfactants, and zwitterionic surfactants.

4. A composition according to claim 1, wherein said at least one washing base is present in a weight content ranging from 4% to 50% by weight, relative to the total weight of said composition.

5. A composition according to claim 1, wherein said at least one washing base is present in a weight content ranging from 6% and 25% by weight, relative to the total weight of said composition.

6. A composition according to claim 1, wherein said at least one anionic polycondensate is formed by an arrangement of blocks, said arrangement of blocks being obtained from:
(1) at least one compound which contains at least two active hydrogen atoms per molecule;
(2) at least one diol or a mixture of diols containing acid radicals or salts thereof; or
(3) at least one di- or polyisocyanate.

7. A composition according to claim 6, wherein said at least one compound (1) is chosen from diols, diamines, polyesterols, polyetherols and a mixture thereof.

8. A composition according to claim 6, wherein said at least one compound (2) is a 2,2-hydroxymethylcarboxylic acid.

9. A composition according to claim 6, wherein said at least one compound (3) is chosen from hexamethylene diisocyanate, tolylene diisocyanate, diphenylmethane 4,4'-diisocyanate, dicyclohexylmethane 4,4'-diisocyanate, methylenebis(p-phenyl) diisocyanate, methylenebis(4-cyclohexyl isocyanate), isophorone dusocyanate, toluene diisocyanate, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanate, 2,2'-dichloro-4,4'-diisocyanatodiphenylmethane, 2,4-dibromo-1,5-diisocyanatonaphthalene, butane-1,4-diisocyanate, hexane-1,6-diisocyanate and cyclohexane-1,4-diisocyanate.

10. A composition according to claim 6, wherein said at least one anionic polycondensate is formed from at least one additional compound having a silicone skeleton.

11. A composition according to claim 10, wherein said at least one additional compound having a silicone skeleton is chosen from polysiloxanes, polyalkylsiloxanes and polyarylsiloxanes.

12. A composition according to claim 11, wherein said at least one additional compound having a silicone skeleton is chosen from polyethylsiloxanes, polymethylsiloxanes and polyphenylsiloxanes.

13. A composition according to claim 12, wherein said at least one additional compound having a silicone skeleton comprises hydrocarbon-based chains grafted onto the silicon atoms.

14. A composition according to claim 1, wherein said at least one polyurethane sequence, said at least one polyurea sequence or said mixture thereof contain a base repeating unit corresponding to the general formula (I') below:

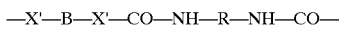 (I')

in which:

the X' radicals, which may the identical or different, are chosen from O and NH, B is a substituted or unsubstituted hydrocarbon-based radical, and R is a divalent radical chosen from aromatic alkylene radicals, ($C_1$ to $C_{20}$) aliphatic alkylene radicals, and ($C_1$ to $C_{20}$) cycloaliphatic alkylene radicals, said alkylene radicals being substituted or unsubstituted.

15. The composition according to claim 14, wherein B is a divalent ($C_1$ to $C_{30}$) hydrocarbon-based radical.

16. A composition according to claim 14, wherein R is chosen from hexamethylene, 4,4'-biphenylene-methane, 2,4-tolylene, 2,6-tolylene, 1,5-naphthylene, p-phenylene-4,4-bis(cyclohexyl) radicals, methylene-4,4-bis(cyclohexyl) radicals, the divalent radical derived from isophorone, and mixtures thereof.

17. A composition according to claim 1, wherein said at least one anionic polycondensate comprises a base repeating unit corresponding to formula (II'):

 (II')

in which:

P is a polysiloxane segment, the X' radicals, which may the identical or different, are chosen from O and NH, and R is a divalent radical chosen from aromatic alkylene radicals, ($C_1$ to $C_{20}$) aliphatic alkylene radicals, and ($C_1$ to $C_{20}$) cycloaliphatic alkylene radicals, said alkylene radicals being substituted or unsubstituted.

18. A composition according to claim 1, wherein said at least one cationic polymer is chosen from:
(1) homopolymers or copolymers derived from acrylic or methacrylic esters or amides and comprising at least one of the units of the following formulae:

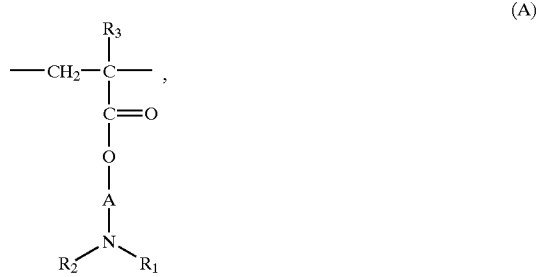 (A)

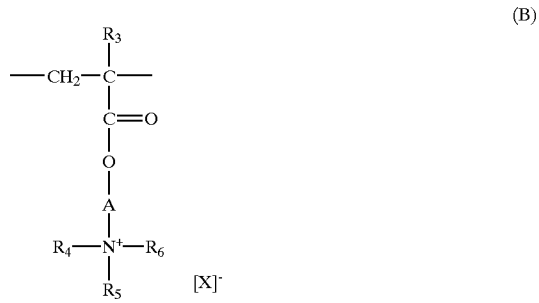 (B)

(C)

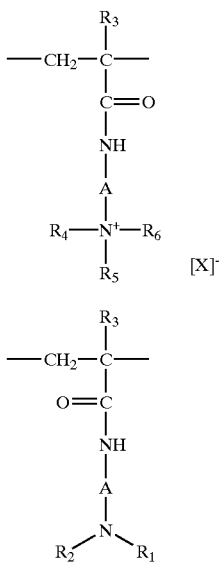

(D)

in which:

R$_3$, which may be identical or different, is chosen from a hydrogen atom and a CH$_3$ radical;

A, which may be identical or different, is chosen from a linear or branched alkyl group of 1 to 6 carbon atoms, or a hydroxyalkyl group of 1 to 4 carbon atoms;

R$_4$, R$_5$ and R$_6$, which may be identical or different, are chosen from an alkyl group containing from 1 to 18 carbon atoms and a benzyl radical;

R$_1$ and R$_2$, which may be identical or different, are chosen from hydrogen and an alkyl group containing from 1 to 6 carbon atoms; and X is an anion derived from an inorganic or organic acid;

(2) cellulose ether derivatives containing quaternary ammonium groups;

(3) cationic cellulose derivatives;

(4) cationic polysaccharides;

(5) polymers comprising piperazinyl units and divalent alkylene or hydroxyalkylene radicals containing straight or branched chains, as well as the oxidation and quaternization products of these polymers;

(6) water-soluble polyamino amides;

(7) polyamino amide derivatives resulting from the condensation of polyalkylene polyamines with polycarboxylic acids followed by alkylation with difunctional agents;

(8) polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms;

(9) cyclopolymers of alkyldiallylamine or of dialkyldiallylammonium;

(10) quaternary diammonium polymer containing repeating units corresponding to the formula:

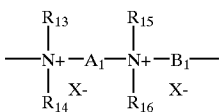

(VII)

in which:

R$_{13}$, R$_{14}$, R$_5$ and R$_{16}$, which may be identical or different, are chosen from aliphatic, alicyclic and arylaliphatic radicals containing from 1 to 20 carbon atoms and lower hydroxyalkylaliphatic radicals, or alternatively R$_{13}$, R$_{14}$, R$_{15}$ and R$_{16}$, together or separately, constitute, with the nitrogen atoms to which they are attached, heterocycles optionally containing a second heteroatom other than nitrogen, or alternatively R$_{13}$, R$_{14}$, R$_{15}$ and R$_{16}$, which may be identical or different, represent a linear or branched (C$_1$–C$_6$) alkyl radical substituted with a nitrile, ester, acyl or amide group or a group —CO—O—R$_{17}$—D or —CO—NH—R$_{17}$—D where R$_{17}$ is an alkylene and D is a quaternary ammonium group;

A$_1$ and B$_1$ are chosen from polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups; and X$^-$ is chosen from an anion derived from an inorganic and organic acid, A$_1$, R$_{13}$ and R$_{15}$ can form, with the two nitrogen atoms to which they are attached, a piperazine ring; in addition, if A$_1$ denotes a linear or branched, saturated or unsaturated alkylene or hydroxyalkylene radical, B$_1$ can also denote a group (CH$_2$)$_n$—CO—D—OC—(CH$_2$)$_n$— in which n is an integer from 1 to 6, and

D is chosen from:

a) a glycol residue of formula: —O—Z—O—, wherein Z denotes a linear or branched hydrocarbon radical or a group corresponding to one of the following formulae:

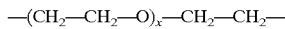

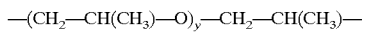

wherein x and y are chosen from an integer from 1 to 4, representing a defined and unique degree of polymerization or any number from 1 to 4 representing an average degree of polymerization;

b) a bis-secondary diamine residue;

c) a bis-primary diamine residue of formula: —NH—Y—NH—, wherein Y denotes a linear or branched hydrocarbon radical, or alternatively the divalent radical

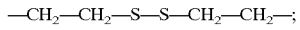

d) a ureylene group of formula: —NH—CO—NH—;

(11) quaternary polyammonium polymers comprising units of formula (VIII):

$$-\underset{\underset{R_{19}}{\overset{R_{18}}{|}}}{N^+}-(CH_2)_r-NH-CO-(CH_2)_q-CO-NH-(CH_2)_s-\underset{\underset{R_{21}}{\overset{R_{20}}{|}}}{N^+}-A- \quad (VIII)$$
$$X^- \qquad\qquad\qquad\qquad\qquad\qquad\qquad\qquad X^-$$

in which:

- $R_{18}$, $R_{19}$, $R_{20}$ and $R_{21}$, which may be identical or different, are chosen from a hydrogen atom a methyl radical, a ethyl radical, a propyl radical, a β-hydroxyethyl radical, a β-hydroxypropyl radical, and a —$CH_2CH_2(OCH_2CH_2)_pOH$ radical, wherein p is equal to 0 or an integer from 1 to 6, with the proviso that $R_{18}$, $R_{19}$, $R_{20}$ and $R_{21}$ do not simultaneously represent a hydrogen atom,

- r and s, which may be identical or different, are integers from 1 to 6,
- q is equal to 0 or an integer from 1 to 34,
- X is a halogen atom, and
- A is a dihalide radical or a —$CH_2$—$CH_2$—O—$CH_2$—$CH_2$— radical;

(12) quaternary polymers of vinylpyrrolidone and of vinylimidazole;

(13) polyamines under the reference name "Polyethylene glycol (15) tallow polyamine" in the CTFA dictionary;

(14) crosslinked polymers of methacryloyloxy($C_1$-$C_4$) alkyltri($C_1$–$C_4$)-alkylammonium salts; and

(15) polyalkyleneimines, condensates of polyamines and of epichlorohydrin, quaternary polyureylenes and chitin derivatives.

19. A composition according to claim 18, wherein said cationic cellulose derivatives are chosen from cellulose copolymers and cellulose derivatives grafted with a water-soluble monomer of quaternary ammonium.

20. A composition according to claim 18, wherein said polymers comprising piperazinyl units and divalent alkylene or hydroxyalkylene radicals containing straight or branched chains are interrupted by oxygen, sulphur or nitrogen atoms or by aromatic or heterocyclic rings.

21. A composition according to claim 18, wherein said water-soluble polyamino amides are prepared by polycondensation of an acidic compound with a polyamine.

22. A composition according to claim 21, wherein said water-soluble polyamino amides are crosslinked with a crosslinking agent chosen from an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide, and an oligomer resulting from the reaction of a difunctional compound which is reactive with a bis-halohydrin, a bis-azetidinium, a bis-haloacyidiamine, a bis-alkyl halide, an epihalohydrin, a diepoxide or a bis-unsaturated derivative.

23. A composition according to claim 22, wherein said crosslinking agent is used in an amount ranging from 0.025 to 0.35 mol per amine group of said polyamino amides.

24. A composition according to claim 23, wherein said polyamino amides are alkylated or, if said polyamino amides contain one or more tertiary amine functions, said polyamino amides are quaternized.

25. A composition according to claim 18, wherein said bis-secondary diamine residue in said quaternary diammonium polymer (10) is a piperazine derivative.

26. A composition according to claim 18, wherein A in said quaternary polyammonium polymers (11) is —$CH_2$—$CH_2$—O—$CH_2$—$CH_2$—.

27. A composition according to claim 18, wherein said polyalkyleneimines are chosen from polyethyleneimines, polymers containing vinylpyridine units and polymers containing vinylpyridinium units.

28. A composition according to claim 1, wherein said at least one cationic polymer is chosen from quaternary cellulose ether derivatives, cyclopolymers, cationic polysaccharides, and vinylpyrrolidone/methacrylamidopropyldimethylamine copolymers.

29. A composition according to claim 1, wherein said at least one cationic polymer is present in a weight content ranging from 0.01% to 10% by weight, relative to the total weight of said composition.

30. A composition according to claim 29, wherein said at least one cationic polymer is present in a weight content ranging from 0.05 to 5% by weight, relative to the total weight of said composition.

31. A composition according to claim 1, wherein said at least one anionic polycondensate is present in a weight content ranging from 0.05% to 10% by weight, relative to the total weight of said composition.

32. A composition according to claim 31, wherein said at least one anionic polycondensate is present in a weight content ranging from 0.1% to 5% by weight, relative to the total weight of said composition.

33. A composition according to claim 1, wherein said composition has a pH ranging from 4 and 9.

34. A method for improving the styling effect of a detergent hair composition containing at least one cationic polymer comprising providing to said detergent hair composition at least one anionic polycondensate comprising at least one polyurethane sequence, at least one polyurea sequence, and mixtures thereof, said at least one anionic polycondensate being water-soluble.

35. A method for cleansing and/or caring for and/or conditioning and/or styling keratin substances comprising applying to said keratin substances a composition comprising:
- at least one washing base,
- at least one cationic polymer,
- at least one anionic polycondensate comprising at least one polyurethane sequence, at least one polyurea sequence, and mixtures thereof,
- said at least one anionic polycondensate being water-soluble.

* * * * *